United States Patent
Katsuura et al.

(12) 
(10) Patent No.: US 7,132,397 B1
(45) Date of Patent: Nov. 7, 2006

(54) BONE MORPHOGENETIC PROTEIN ANTAGONIST BASED ON THE MATURE PROTEIN

(75) Inventors: Mieko Katsuura, Tokyo (JP); Michio Kimura, Kanagawa (JP)

(73) Assignee: Biopharm Gesellschaft zur biotechnologischen Entwicklung von Pharmaka mbH, Heidelberg (DE)

( * ) Notice: Subject to any disclaimer, the term of this patent is extended or adjusted under 35 U.S.C. 154(b) by 0 days.

(21) Appl. No.: 09/806,368

(22) PCT Filed: Oct. 4, 1999

(86) PCT No.: PCT/IB99/01621

§ 371 (c)(1),
(2), (4) Date: Sep. 20, 2001

(87) PCT Pub. No.: WO00/21998

PCT Pub. Date: Apr. 20, 2000

(30) Foreign Application Priority Data

Oct. 9, 1998 (JP) .................................. 10-288103

(51) Int. Cl.
*A61K 38/18* (2006.01)
*C07K 14/51* (2006.01)

(52) U.S. Cl. .................. 514/12; 530/350; 530/403; 530/404

(58) Field of Classification Search .............. 530/350, 530/402; 435/69.1; 514/2
See application file for complete search history.

(56) References Cited

FOREIGN PATENT DOCUMENTS

EP 0691349 1/1996

OTHER PUBLICATIONS

Hirsinger et al. (1997), "Noggin acts downstream of Wnt and Sonic Hedgehog to antagonize BMP4 in avian somite patterning," Development 124: 4605-4614.*
Xiao et al. (2002), J. Bone Miner. Res. 17(1): 101-110.*
Wozney (1992), Mol. Reprod. Dev. 32: 160-167.*
Canalis et al. (2003), Endocrine Reviews 24: 218-235.*
Yamashita et al. (1996), Bone 19(6): 569-574.*
Strange et al. (2002), Clinical Science 102: 253-268.*
Massagué (1998), Annu. Rev. Biochem. 67: 753-791.*

* cited by examiner

*Primary Examiner*—David S. Romeo
(74) *Attorney, Agent, or Firm*—Rothwell, Figg, Ernst & Manbeck, P.C.

(57) ABSTRACT

The purpose is to provide a mature protein having an antagonistic activity against bone morphogenetic proteins. The mature protein having an antagonistic activity against bone morphogenetic proteins is obtained by converting at least one residue among methionine residues or tryptophane residues existing in the amino acid sequence of mature human MP52 (SEQ ID No 1) to a hydrophilic residue by chemical modification, or replacing said residues with a hydrophilic amino acid residue or a polar amino acid residue. The chemical modification for said methionine residue is performed by an oxidization reaction or an alkylation reaction. The chemical modification for said tryptophane residue is performed by an allylsulphenylation reaction. Or a mature protein having an antagonistic activity against bone morphogenetic proteins is obtained by converting at least one residue of tryptophane residues existing in the amino acid sequences of mature human BMP-2 (SEQ ID No 2), mature human BMP-4 (SEQ ID No 3), and mature human BMP-7 (SEQ ID No 4) to a hydrophilic residue by chemical modification, or replacing said residues with a hydrophilic amino acid residue or a polar amino acid residue.

24 Claims, 2 Drawing Sheets

BONE MORPHOGENETIC PROTEIN ANTAGONIST BASED ON THE MATURE PROTEIN

This application is a 371 of PCT/IB99/01621 filed Oct. 4, 1999.

BACKGROUND OF THE INVENTION (1) Field of the Invention

This invention relates to a mature bone morphogenetic protein of which some hydrophobic amino acid residues are exchanged to a hydrophilic or a polar amino acid residue by chemical modification or genetic engineering technology. The mature proteins of this invention show an antagonistic activity against bone morphogenetic proteins, and are useful for medicinal agents to suppress symptoms of ectopic osteogenesis and ectopic calcification or metabolic bone diseases with calcification such as neurotic osteosis, ectopic ossification caused by stress of operation, traumatic myositis ossificans, ossification by defect of oxygen supply, osteogenic tumor, ossification of the posterior longitudinal ligament, and arterial sclerosis.

(2) Description of the Related Art

A bone morphogenetic protein (hereinafter called BMP) is a protein having a bone morphogenetic activity in decalcified bone tissue. Although the isolation of BMP had been worked on energetically since the 1970s, it was quite difficult to isolate as a single protein. Gene cloning of BMP as expected was performed by Wozney in 1989 by molecular biological technology, using the amino acid sequences derived from unknown peptides which were separated by treating the fraction having bone morphogenetic activities with an enzyme. The gene was immediately introduced to the animal cultured cells, and the activity of the protein expressed was measured in vivo, and BMP activity in the protein was practically proved (Wang, E. A. et al., (1990) Proc. Natl. Acad. Sci. USA, vol. 87, p. 2220–2224). Continuing cloning a protein with bone morphogenetic activities utilizing homology, several numbers of the proteins with bone morphogenetic activities in a similar structure have been isolated so far. Those proteins all belong to TGF (transforming growth factor)-β superfamily and are proved to have the activity to cause ectopic ossification in vivo, basically. Ossification caused by BMP is said to be internal cartilaginous and it seems to reproduce the formation of long bone at an embryonal stage. Therefore, BMP itself can be used as a medicinal agent for the treatment to compensate the bone deficit.

On the other hand, since BMP genes were disclosed and the specific antibodies against BMPs were prepared, BMPs were also expressed at the site of ectopic calcification, which have not had any medical treatment so far, and there seem some possibilities of the relationship between BMPs and those diseases. For example, it becomes recently evident that BMP exists or is included in diseases such as neurotic osteosis, ectopic ossification caused by stress of operation, traumatic myositis ossificans, ossification by defect of oxygen supply, osteogenic tumor, specified as refractory diseases such as ossification of the posterior longitudinal ligament (OPLL) (Spine, 17-3S, S33, 1992) and calcification part of arterial sclerosis (J. Clin. Invest., vol. 91, p. 1800, 1993). In addition, the major symptoms of pseudomalignant heterotopic ossification (PHO), pseudomalignant osseous tumor and myosistis ossificans circumscripta are ache and the appearance of the hard tissue mass in the muscle. Though the causes of these diseases are still unknown in detail, BMP seems to have a relationship with the appearance of hard tissue in the muscle of the patients. It is considered that BMP exists in the tissue in which BMP does not exist naturally, acts on autocrine, and forms bone like hard tissue. There is no effective treatment for OPLL by now. When the compressive neural symptom is critical, an excision is operated. However the prognosis is not so good. There is no treatment for calcification of artery, neither.

It seems that suppression of BMP existence may be one of the major treatments for these diseases. Another treatment, such as administration of BMP antagonists, also seems effective. BMP receptors, neutralized antibodies against BMP and the BMP peptides corresponding to the binding site, a BMP with chemically modified specific amino acid residue are thought to have BMP antagonist-like activity.

Many studies have been so far carried out concerning a relationship between the structure and the activity of BMPs and it is speculated that some sites of mature BMPs relate to the receptor binding. It is known that a peptide synthesized based on these studies works as an antagonist against BMPs (JP patent application, Hei 7 ('95)-200175).

SUMMARY OF THE INVENTION

Other than the synthetic peptides, many kinds of methods are desired to exist for therapy of various diseases of bones and cartilages such as hyperplasia. The purpose of this invention is to provide a new BMP antagonist protein as an effective therapeutic agent for above bone-related diseases in which a specific amino acid residue is chemically modified or replaced by genetic engineering technology.

DESCRIPTION OF THE PREFERRED EMBODIMENT

Figure 1:
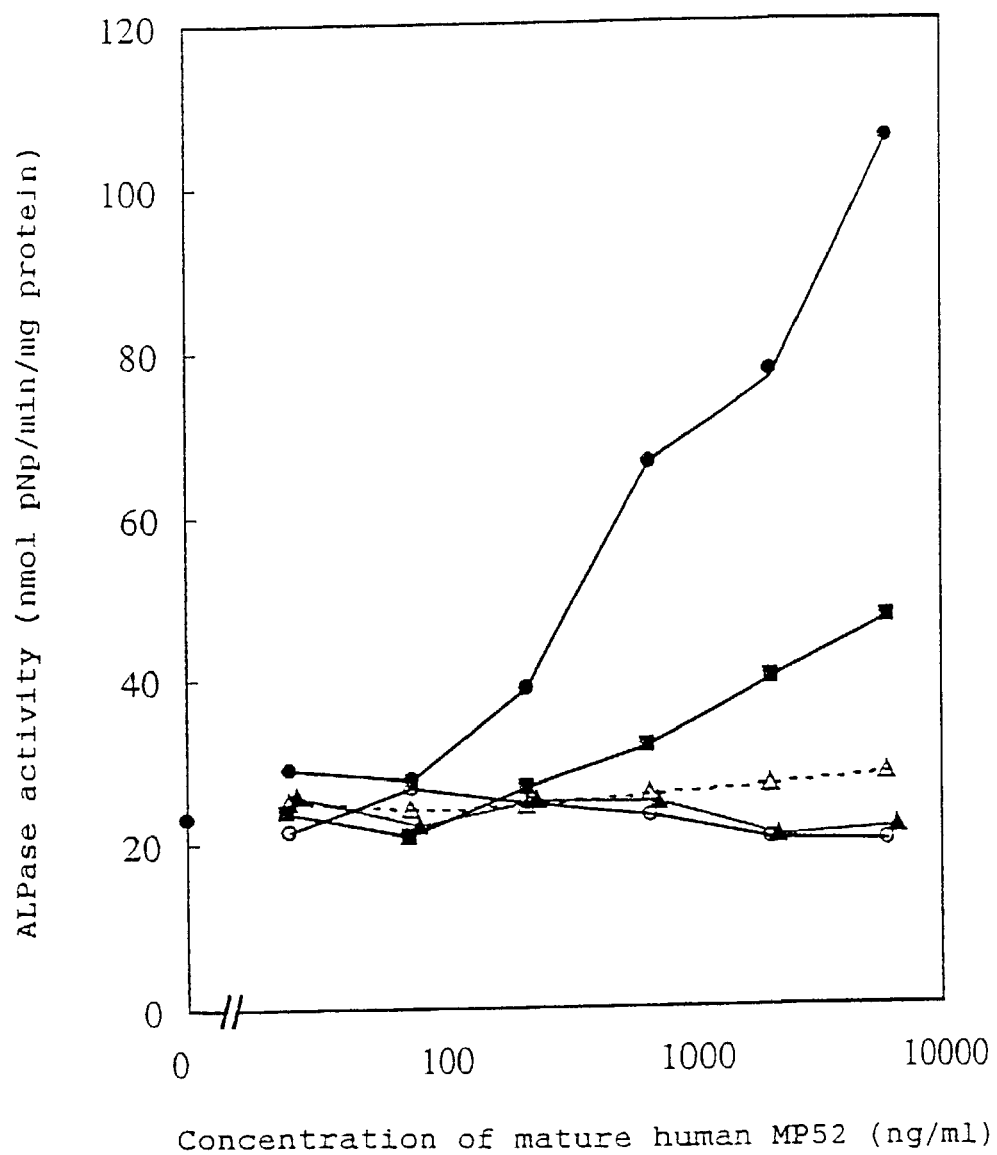
FIG. 1 shows a comparison of ALPase inducing activities by methionine alkylated mature human MP52s and that of unmodified mature human MP52 in MC3T3-E1 cells, which were separated by the difference in the retention time on the reverse chase HPLC. In the figure, the solid line with solid circles represents unmodified mature human MP52, the solid line with solid squares represents one-methionine alkylated mature human MP52, the broken line with solid triangles represents two-methionine alkylated mature human MP52, the solid line with open circles represents three-methionine alkylated mature human MP52, the dotted line with open triangles represents four-methionine alkylated mature human MP52, respectively. The solid circles shown in of the Y-axis represents ALPase activity in cells without treated by any reagent.

The present invention relates to a mature protein having an antagonistic activity against bone morphogenetic proteins, obtained by converting at least one residue among methionine residues or tryptophane residues existing in the amino acid sequence of mature human MP52 (SEQ ID No 1) to a hydrophilic residue by chemical modification, or replacing said residues with a hydrophilic amino acid residue or a polar amino acid residue by genetic engineering technology.

When at least one residue of said methionine is converted, chemical modification for said methionine residue is an oxidization reaction or an alkylation reaction.

When the chemical modification of said methionine residue is an oxidization reaction, among the preferred mature proteins of the invention is chat in which four methionine residues are oxidized and having the amino acid sequence of SEQ ID No 5.

When the chemical modification of said methionine residue is an alkylation reaction, among the preferred mature proteins of the invention is that in which at least one methionine residue is S-carboxymethylated and having the amino acid sequence of SEQ ID No 6.

When at least one residue of said tryptophane is converted, chemical modification for said tryptophane residue is an allylsulphenylation reaction.

Among the Preferred mature proteins of the invention is that in which two tryptophane residues are allylsulphenylated and having the amino acid sequence of SEQ ID No 7.

The present invention relates to mature proteins of the invention as defined above having an antagonist activity against bone morphogenetic proteins wherein said mature human MP52 is a dimer protein.

Further, the present invention relates to a mature protein having an antagonistic activity against bone morphogenetic proteins, obtained by converting at least one residue of tryptophane residues existing in the amino acid sequence of mature human BMP-2 (SEQ ID No 2), mature human BMP-4 (SEQ ID No 3), or mature human BMP-7(SEQ ID No 4) to a hydrophilic residue by chemical modification, or replacing said residues with a hydrophilic amino acid residue or a polar amino acid residue by genetic engineering technology.

Furthermore, the present invention relates to a mature protein having an antagonistic activity against bone morphogenetic proteins, obtained by replacing at least one amino acid residue of three hydrophobic amino acid residues, among said hydrophobic amino acid residues relating to a receptor binding site in the amino acid sequence of mature human BMP-2 (SEQ ID No 2), mature human BMP-4 (SEQ ID No 3), or mature human BMP-7 (SEQ ID No 4), which are located in positions corresponding to those of methionine residues located in 30th, 71st, and 74th positions of the amino acid sequence of mature human MP52 (SEQ ID No 1), with a hydrophilic amino acid residue or a polar amino acid residue by genetic engineering technology.

The present invention relates to mature proteins of the invention as defined above having an antagonist activity against bone morphogenetic proteins, wherein said mature human BMP-2, mature human BMP-4 or mature human BMP-7 is a dimer protein.

The present invention, further, relates to an agent for therapy and/or prevention of ectopic ossification, containing a mature protein of the invention defined above as an effective ingredient showing an antagonistic activity against bone morphogenetic proteins.

Furthermore, the present invention relates to an agent for therapy and/or prevention of metabolic diseases with calcification, containing a mature protein of the invention defined above as an effective ingredient showing an antagonistic activity against bone morphogenetic proteins.

The proteins belonging to the TGF-β superfamily are each presumed from its gene structure to be synthesized as a precursor in cells and to be formed into a mature (active type) peptide homodimer after various processings. The active type of mature human TGF-β1 is known to be a dimer of the peptide of COOH-terminal 112 residues (Nature, 316, 701–705, 1985). The term "mature BMP" as used herein means a BMP which is substantially composed of an amino acid sequence homologous with COOH-terminal 112 amino acid residues of active type of human TGF-β1. The proteins belonging to the TGF-β superfamily in the present invention are exemplified as BMP-2, BMP-4, BMP-7, human MP52 and so on.

The inventors attempted a chemical modification and a replacement with an amino acid for human MP52 that belongs to TGF-β superfamily and particularly that is a member of BMP family, with a purpose of preparing a chemically modified protein strongly acting as a BMP antagonist through binding to BMP binding site on the receptor.

It is assumed that the activated type of human MP52 is a dimer form and that the receptor binding site of mature MP52 is an exposed part on the outside of the protein molecule. Thus, the receptor binding site is speculated that it is composed of two vicinal peptide regions (the amino acid positions from the 20th Arg to the 38th Ala and from 60th Glu to 77th Glu in SEQ ID No 1 of the Sequence Listing) in formation of a dimer of human MP52.

We prepared a protein of which two kinds of amino acid residues were chemically modified because it is known that the content of tryptophan and methionine is generally low in amino acid composition of the protein allowing selective chemical modification, and from the assumed three-dimensional structure of human MP52 that three (30th, 71st, and 74th positions) of four methionine residues in the monomer of mature human MP52 exist in the assumed receptor binding site and that both (32nd and 35th) of two tryptophane residues in the monomer of mature human MP52 exist in the assumed receptor binding site of mature MP52.

Chemical modification of this intention means that the side chains of methionine or tryptophane are modified in a degree enough to make the protein inactive with keeping a binding ability to the receptor. For the chemical modification, a conventional method in studies on protein chemistry is applied. The method is described in "Protein Chemistry IV," pp 6–118, 1977, Jap. Soc. Biochem. Methionine is a hydrophobic amino acid and can be modified into a hydrophilic residue by chemical modification. Chemical modifications in increasing hydrophilicity are exemplified by oxidization of methionine to make methionine sulfoxide or methionine sulfon using an oxidant and by alkylation to make S-carboxymethylmethionine using α-halogenoacetic acid. The oxidization of methionine are performed by hydrogen peroxide, performic acid, periodic acid, N-chlorosuccinimide, and N-bromosuccinimide. Besides, for α-halogenoacetic acid, monoiodoacetic acid and monoiodoacetamide can be used.

Chemical modification to indole ring of tryptophane gives a subtle change of environment and structure nearby it. Suitable examples are allylsulphenylation of the second position of indole nucleus by p- or o-nitrophenyl-sulphenylchloride, 2-nitro-4-carboxyphenylsulphenylchloride, 2,4-dinitrophenylsulphenylchloride, or 2-hydroxy-5-nitrobenzylation of the 3rd position of indole nucleus by 2-hydroxy-5-nitrobenzylbromide, dimethyl(2-hydroxy-5-nitrobenzyl) sulfonylbromide.

The present invention in particular relates to a mature protein of which one to 4 methionine residues or 1 to 2 tryptophane residues are chemically modified in mature human MP52 amino acid sequence shown in SEQ ID No 1 of the Sequence Listing.

The protein shown in SEQ ID No 1 of the Sequence Listing can be produced by the method described in international Patent Application WO 96/33215. Since 3 out of 4 methionine residues exist in the receptor binding site of mature human MP52 produced by said method, and all 2 tryptophane residues exist there, and whose amino acids are all hydrophobic, it is assumed that these hydrophobic amino acids play an important role in bone morphogenetic activity.

Mature human MP52 of the present invention includes not only the mature protein with the amino acid sequence shown in SEQ ID No 1 of the Sequence Listing but also Ala or Arg-Ala binding to the N-terminus of the amino acid sequence of said mature protein as disclosed respectively in international patent application WO 95/04819 and WO 97/06254.

Comparing the amino acid sequences of the mature proteins of other BMPs such as human BMP-2 (SEQ ID No 2), human BMP-4 (SEQ ID No 3), human BMP-7 (SEQ ID No 4) and so on with that of mature human MP52 protein, it is found that in those bone morphogenetic proteins the amino acids corresponding to the positions of methionine residues of mature human MP52 are all methionine residues or hydrophobic amino acids.

In concrete, the receptor binding site of mature human BMP-2 is estimated to be the peptides with the amino acid sequence from 16th Arg to 34th Ala and from 56th Asn to 73th Lys shown in SEQ ID No 2 of the Sequence Listing (Science 242, 1528–1534, 1988). The amino acids of mature human BMP-2, which corresponds to methionines' position of the mature human MP52 (30th, 71st and 74th), are replaced with 26th Val, 67th Val and 70th Val.

The receptor binding site of mature human BMP-4 is estimated to be the peptides with the amino acid sequence from 18th Arg to 36th Ala and from 58th Asn to 75th Ser shown in SEQ ID No 3 of the Sequence Listing (DNA Seq. 5 (5), 272–275, 1995). The amino acids of mature human BMP-4, which corresponds to methionines' position of mature human MP52 (30th, 71st and 74th), are replaced with 28th Val, 69th Val and 72rd Val.

The receptor binding site of mature human BMP-7 is estimated to be the peptides with the amino acid sequence from 40th Lys to 58th Ala and from 80th Asn to 97th Glu shown in SEQ ID No 4 of the Sequence Listing (Proc. Natl. Acad. Sci. U.S.A. 93(2), 878–883, 1996). The amino acids of mature human BMP-7, which corresponds to methionines' position of mature human MP52 (30th, 71st and 74th), are replaced with 50th Leu, 91st Val and 94th Ile.

It is difficult to carry out a chemical modification selectively on the hydrophobic amino acids of which positions correspond to those of methionine of mature human MP52. However, it is possible to replace hydrophobic amino acids with hydrophilic or polar amino acids by genetic engineering technology.

Since the tryptophane residues are conserved in all BMPs described above, it is possible to replace hydrophobic amino acids with hydrophilic or polar amino acids by chemical modification method or genetic engineering technology. The tryptophane residues also play an important role in making a change in a three-dimensional structure in chemical modification and genetic engineering technology.

Thus, the present invention relates to mature human MP52, in particular, which is obtained by converting one to 4 methionine residues or one to 2 tryptophane residues existing in the amino acid sequence shown in SEQ ID No 1 of the Sequence Listing to hydrophilic residues or polar amino acid residues by recombinant engineering technology. In the present invention hydrophilic amino acids and polar amino acids are aspartic acid, glutamic acid, lysine, arginine, histidine, serine, threonine and so on. In the present invention, when methionine residues or tryptophane residues are converted to other hydrophilic or polar amino acids, the protein of the present invention can be obtained by transforming a recombinant DNA into E. coli which are made by replacing the codons corresponding to methionines at 30th, 71st, 74th and 111th positions or the codons corresponding to tryptophanes at 32nd and 35th positions shown in SEQ ID No 1 replaced with the codons of aspartic acid, glutamic acid, lysine, arginine, histidine, serine, threonine and so on or by making.

Further, the present invention relates to any mature proteins having the amino acid sequence shown in SEQ ID Nos 2 to 4, of which one to two tryptophane residues are subjected to chemical modification.

The present invention furthermore relates to any mature proteins having the amino acid sequence shown in SEQ ID Nos 2 to 4, in which hydrophobic amino acids consisting of the receptor binding site, 1 to 3 hydrophobic amino acids corresponding to the positions of 30th, 71st and 74th methionine residues or 1 to 2 tryptophane residues are replaced with hydrophilic amino acids or polar amino acids. In the present invention, hydrophobic amino acids are methionine, valine, leucine, isoleucine or tryptophane.

The present invention relates to the mature protein having the amino acid sequence shown in SEQ ID No 5 of the Sequence Listing, in which 4 methionine residues of the methionine residues are oxidized. In detail, for the oxidization of methionine residue, hydrogen peroxide is added at a final concentration of 0.014% to 2 mg/ml of the mature protein and the reaction is carried out for more than 15 hours at room temperature and then the mature protein of which methionine residues are in methionine sulfoxide can be obtained.

The present invention relates to the mature protein having the amino acid sequence shown in SEQ ID No 6 of the Sequence Listing, in which 1 to 4 methionine residues of the methionine residues are alkylated. In detail, monoiodoacetic acid is added at a concentration of higher than methionine residues by 50 to 100 at the molar ratio to 2 mg/ml of the mature protein and the reaction is carried out for more than 15 hours at room temperature and then the mature protein of which methionine residues are S-carboxymethylated can be obtained.

The present invention relates to the mature protein having the amino acid sequence shown in SEQ ID No 7 of the Sequence Listing, in which 2 tryptophane residues of the trypophane residues are allylsulphenylated. In detail, 20 equivalents of p-nitrophenylsulphenyl chloride in 100% acetic acid is added to 2 mg/ml of the mature protein and the reaction is carried out for 1 hour at room temperature and then the mature protein of which tryptophane residues are allylsulphenylated can be obtained.

The present invention relates to the mature protein having an amino acid sequence shown in SEQ ID No 2 of the Sequence Listing, in which 1 to 2 tryptophane residues at 28th and 31st are allylsulphenylated.

The present invention relates to the mature protein having an amino acid sequence shown in SEQ ID No 2 of the Sequence Listing, in which one or all of 26th, 67th and 70th valine residues or one or both of 28th and 21st tryptophane residues are replaced with aspartic acid, glutamic acid, lysine, arginine, histidine, serine, threonine and so on.

The present invention relates to the mature protein having an amino acid sequence shown in SEQ ID No 3 of the Sequence Listing, in which one or both of 30st and 33th tryptophane residues are allylsulphenylated.

The present invention relates to the mature protein having an amino acid sequence shown in SEQ ID No 3 of the Sequence Listing, in which one or all of 28th, 69th and 72rd valine residues or one or both of 30st and 33th tryptophane residues are replaced with aspartic acid, glutamic acid, lysine, arginine, histidine, serine, threonine and so on.

The present invention relates to the mature protein having an amino acid sequence shown in SEQ ID No 4 of the Sequence Listing, in which one or both of 52nd and 55th tryptophane residues are allylsulphenylated.

The present invention relates to she mature protein having an amino acid sequence shown in SEQ ID No 4 of the Sequence Listing, in which one or all of 50th leucine, 91st valine, 94th isoleucine, 131th methionine or one or both of 52nd and 55th tryptophane residues are replaced with aspartic acid, glutamic acid, lysine, arginine, histidine, serine, threonine and so on.

The BMP antagonist-like activity of the protein modified chemically or replaced with other amino acids in the present invention can be proved by measuring alkaline phosphatase (ALPase) activity as a marker of biological activity by adding in a culture medium of a murine carvarial clonal cell line (MC3T3-E1 cell) having osteoblastic property which Kodama et al. established (Kodama, H. et al. (1981) Jpn. J. Oral Biol., vol. 23, p. 899). ALPase is often used as a marker enzyme for differentiation/maturation in osteoblasts and cartilage cells (Pfeilschifter, J., et al., Endocrinology (1987), vol. 121, p 212–218; Rodan, G. A., et al., Calcium regulating hormones and bone metabolism, Elsevier Science Publishers B.V., (1992), p 183–196).

The mature protein obtained by examples 1 to 3 in the present invention inhibited dose-dependently the increase of ALPase activities which were induced by recombinant mature human BMP-2 (rh-BMP-2) or mature human MP52 in MC3T3-E1 cell line and C3H10T ½ cell line having osteoblastic property. The result indicated that the protein in the present invention could inhibit not only the activity of human MP52 but also the activities of other BMPs.

The present invention relates to an agent for therapy and/or prevention of ectopic ossification, containing any protein described above as an effective ingredient.

Furthermore, the present invention relates to an agent for therapy and/or prevention of metabolic diseases with calcification, containing any mature protein described above as an effective ingredient.

The protein of the present invention is effective in therapy as an agent of suppressing worsening condition of OPLL and arterial sclerosis, treating tumor in bone and cartilage in which BMP is expressed and treating other metabolic bone diseases. It can suppress worsening condition by lowering the function of osteoblasts by using over cycle of metabolic bone such as Paget's disease. It can also be useful as a reagent for screening or evaluating systems of medicinal agents which compete with BMP and the receptor binding.

The administrating method can be exemplified as intravenous and intramuscular administrations. Not only a standard intravenous injection but also intravenous drip infusion can be applied to intravenous administration.

For example, it can be prepared as a powder preparation for injection. In this case, one or more than two kinds of water soluble excipients such as mannitol, sugar, lactose, maltose, glucose and fructose may be added to the agent and dissolved in water. And after putting the mixture into vials or ampoules, they are freeze-dried and then sealed to be an injection preparation.

Although the adult clinical administration dosage for a day may vary from and also depend on administrating methods, ages, weigh, conditions of patients and so on, it is usually 0.01–5 mg of the protein.

This invention is described in detail by examples written below. However, this invention is not restricted to these examples.

EXAMPLES

Example 1

Preparation of Mature Human MP52 of which Methionine Residue is Oxidized (1) Oxidization of Methionine Residue of Mature Human MP52 by Hydrogen Peroxide (Conversion to Methionine Sulfoxide)

Hydrogen peroxide was added to mature human MP52 (2 mg/ml concentration) dissolved in 2 mM EDTA–10 mM hydrochloric acid at the final concentration of 0.014% and the solution was reacted at room temperature for more than 15 hours.

(2) Separation of Methionine Oxidized Mature Human MP52

Mature human MP52 having the amino acid sequence shown in SEQ ID NO 1 (hereinafter, unmodified mature human MP52) and methionine oxidized mature human MP52 having the amino acid sequence of SEQ ID NO 5 were separated by using reverse phase HPLC on the basis of a difference between retention times of both proteins. Oxidization increased a hydrophilic property of the proteins and retention time methionine oxidized mature human MP52 on the reverse phase HPLC becomes faster than that of unmodified mature human MP52. The conditions of separation are as follows. For column, NUCLEOSIL™ 5-C18-300 column (4.6 mm I.D.×150 mm, silica material having a particle size of 5 microns, a carbon content of 18% and a pore size of 300 Å, GL Science Corp.) was used at the flow rate of 1.3 ml per minute at 45° C.: absorbance at 214 nm and 280 nm were measured to detect peaks. For solvent, water containing 0.05% TFA as solution A and acetonitrile containing 0.05% TFA as solution B were used. Elution of proteins were performed with a linear gradient of solution B from 25% to 45% for 80 minutes using an HPLC pump, HP1050

Under this condition, unmodified mature human MP52 is eluted at around 51 minutes, whereas methionine oxidized mature human MP52 was eluted at around 47 minutes. Thus, both were easily separated.

(3) Determination of the Oxidization of Methionine Residue

The oxidization of methionine residue was detected by comparating elution patterns of the reverse phase column chromatography of trypsin digested fragments of unmodified mature human MP52 and methionine oxidized mature human MP52.

Unmodified mature human MP52 has seven cysteine residues as shown in SEQ ID No 1 of the Sequence Listing. Six out of seven cysteine residues form three intramolecular disulfide bonds and the remaining one cysteine forms a dimer. For complete enzymatic digestion, reducing disulfide bond and blocking SH group are required to inhibit rebinding. For this purpose, dithiothreitol was used to reduce the disulfide bond and the cysteine residue was alkylated (S-carboxy-methylation) before trypsin digestion.

First, lyophilized unmodified mature human MP52 and methionine oxidized mature human MP52 were dissolved in 8 M urea-0.2 M ammonium bicarbonate-2 mM EDTA (pH 8.5) at the final concentration of 1 mg/ml, and 50-fold molar excess of dithiothreitol (DTT) to the cysteine residue was added and reacted at 50° C. for 30 minutes. To this solution, 250-fold molar excess of monoiodoacetamide to the cysteine residue was added and reacted for 30 minutes with shading to yield S-carboxymethylated unmodified mature human MP52 and S-carboxymethylated methionine oxidized mature human MP52. Digestion of these proteins was performed by adding trypsin. After four-fold dilution of this solution with water to make the final urea concentration of 2 M, at the weight ratio of 1/50 to the proteins at 37° C. for 18 hours, the trypsin digestion was applied to the reverse phase HPLC column to separate all fragments. The conditions of separation are as follows. NUCLEOSIL™ 5-C18-300 column (4.6 mm I.D.×150 mm, silica material having a particle size of 5 microns, a carbon content of 18% and a pore size of 300 Å, GL Science Corp.) was used for separation at the flow rate of 1.3 ml per minute at 45° C.; absorbance at 214 nm was measured to detect peaks. For solvent, water containing 0.05% TFA as solution A and acetonitrile containing 0.05% TFA as solution B were used. Elution of peptides was Performed by a linear gradient of solution B from 0% to 45% or 90 minutes after keeping 0% for initial five minutes, using HPLC pump, HP1050 (Hewlett Packard).

Subsequently, amino acid composition analysis was carried out to determine the positions of the digested peptide on the primary structure of reduced alkylated unmodified mature human MP52 and reduced alkylated methionine oxidized mature human MP52. The operation of the amino acid composition analysis was mainly based on Zoku Seikagaku Zikken Kouza (Tokyo Kagaku Doujin), Vol. 2, Protein Chemistry (I), Section 4. Brief description is given below.

Hydrolysis was performed in a vapor of 6 N HCl containing 0.1% phenol at 110° C. for 21 hours by using PICO. TAG. WORK STATION™ (RP-HPLC for amino acid analysis) (Waters). Following this step, the amino acid composition analysis was carried out by PTC method by using Amino acid standard H (Pierce) as a standard amino acid. PTC-amino acids were separated by reverse phase HPLC using HPLC pump (model 510; Waters), a Wakopak WS-PTC (4.0 mm I.D.×200 mm; Wako Pure Chemicals), and solvents of PTC amino acids eluent A and PTC amino acids eluent B (both Wako Pure Chemicals).

The HPLC retention times of the identified trypsin peptides on the primary structures of unmodified and oxidized mature MP52 were compared each other. The trypsin fragments of mature human MP52 containing methionine residues were three kinds corresponding to: position from 29th to 56th (29–56; containing 30th methionine) shown in SEQ ID No 1, position from 57th to 88th (57–88; containing 71st, and 74th methionines) in SEQ ID No 1, and position from 107th to 119th (107–119; including 111th methionine) in SEQ ID No 1. The elution time of respective fragments derived from the reduced alkylated unmodified mature human MP52 were around 84 min, 62 min, and 36 min in order. In comparison, the fragments derived from the reduced alkylated methionine oxidized mature human MP52 (SEQ ID No 5) were around 80 min, 48 min, and 31 min in order showing the earlier elution than that of the fragments derived from the reduced alkylated unmodified mature human MP52.

On the other hand, there was no difference for other fragments which do not contain methionine. As a result, the specific reaction of oxidization to the methionine residues was determined.

Example 2

Preparation of Mature Human MP52 of which Methionine Residue was S-Carboxymethylated (1) Alkylation of Methionine Residue of Mature Human MP52 by Monoiodoacetic Acid Though the highest reactivity of alkylation using monoiodoacetic acid is observed in SH residues of cysteine residue, the alkylation reaction almost selectively occurs in methionine residue in an acidic condition, because all the cysteine residues of unmodified mature human MP52 form disulfide bonds as described before. Therefore, the operation was conducted as follows. Monoiodoacetic acid (molar ratio; 50–100 times higher than moles of methionine residue) was added to unmodified mature human MP52 with a concentration of 2 mg/ml dissolved in 10 mM hydrochloric acid and incubated at room temperature for 3–18 hours.

(2) Separation of Mature Human MP52 of which Methionine Residue was Alkylated

Unmodified mature human MP52 and methionine alkylated mature human MP52 having the amino acid sequence of SEQ ID No 6 were separated on the basis of a difference in retention times between both proteins by using reverse phase HPLC. The conditions of separation (a column employed, a flow rate, wavelengths for detection, and a pump for HPLC) were the same as those of Example 1 (2). For solvent, water containing 0.05% TFA as solution A and acetonitrile containing 0.05% TFA as solution B were used. Elution of the proteins were performed by a linear gradient of solution B from 30% to 45% for 60 minutes after five minutes of an initial condition.

Under this condition, unmodified mature human MP52 is eluted as one peak around 38 minutes and, in contrast to this, alkylated mature human MP52 showed four peaks (elution times: 36 min, 34 min, 32 min, and 29 min) other than one peak around 38 minutes which is the elution time of unmodified mature human MP52. Elution time becomes earlier in accordance with proceeding of the reaction, namely, depending on the increasing number of alkylated methionines. These peaks were collected to identify these proteins by the amino acid composition analysis similar to Example 1 (3). In the amino acid composition analysis, alkylated methionines are detected as a separate peak from unmodified methionines, because alkylated methionines are not decomposed by hydrolysis. Namely, the progress of the reaction can be determined by a decrease in methionine peaks.

By the separation experiment, it was known that the elution peak at 29-min was that of all four methionines alkylated mature MP52, the elution peak at 32-min was that of three methionines alkylated one, the elution peak at 34-min was that of two methionines alkylated one, the elution peak at 36-min was one methionine alkylated one. In addition, the elution peak at around 38-min was known as unalkylated one. Amino acid compositions of these peaks were good agreement with those of theoretical values of mature human MP52 except for the value of methionine. Consequently, it is confirmed that the alkylation reaction to methionine residue occurs specifically and the separated peaks show progressing stages of the alkylation reaction differently.

(3) Determination of the Alkylated Methionine Residues

The alkylated methionine residue was determined by comparing elution patterns of trypsin digested fragments of unmodified mature human MP52 and methionine alkylated mature human MP52 on the reverse phase HPLC.

Similar to Example 1 (3), cysteine residues were blocked by alkylation before trypsin digestion after reduction of disulfide bonds by using dithiothreitol. Since S-carboxymethylation was performed using monoiodoacetic acid for the alkylation of methionine; alkylation of cysteine was performed by using 4-vinyl pyridine as an alkylation reagent for monoiodoacetic acid, which was not similar to Example 1. Alkylation reaction takes place almost selectively in reduced cysteine at pH 8.5, and hardly in methionine. Thus, the reason of employing different alkylation is to detect side reaction in methionine.

First, lyophilized unmodified mature human MP52 and methionine alkylated mature human MP52 were dissolved in a solution of 6 M guanidine-HCl–0.4 M Tris-HCl buffer (pH 8.5) at the final concentration of 1 mg/ml, and reduced with 50-fold excess molar of dithiothreitol (DTT) to the cysteine residues at 50° C. for 30 minutes. S-pyridyl-ethylation was performed by adding 250-fold excess molar of 4-vinyl pyridine to the cysteine residues and incubated for 30 minutes with shading. The solution was applied on a desalting column (PD-10; Pharmacia) equilibrated with a 6 M guanidine-HCl–0.4 M Tris-HCl buffer (pH 8.5) to remove excessive reagent and followed by reverse phase HPLC using a reverse phase column (Cosmasil 10C18-300, 4.6 mm I.D.×100 mm, Nakalai Tesque Inc.). A fraction having both absorption at 280 nm derived from tryptophane and 254 nm derived from pyridine by UV detector was collected.

Following this step, the trypsin digestion was performed by the same method as that of Example 1 (3) to separate digested fragments.

Finally, the position of respective fragments in the primary structure of mature MP52 was determined by the amino acid composition analysis as same as that of Example 1 (3).

Using the reverse phase HPLC, a comparison of elution times of respective trypsin fragments of unmodified mature human MP52 and methionine alkylated mature human MP52 of which position in the primary sequences was determined by the amino acid composition analysis was performed. Trypsin fragments of mature human MP52 containing a methionine residue were three kinds corresponding to: the amino acid position from 29th to 56th (29–56; containing 30th methionine) shown in SEQ ID No 1, the amino acid position from 57th to 88th (57–88; containing 71st and 74th methionines) in SEQ ID No 1, and the amino acid position from 107th to 119th (107–119; containing 111th methionine) in SEQ ID No 1. The elution time of respective fragments derived from unmodified mature human MP52 were around 77 min, 58 min, and 36 min in order. In comparison, fragments derived from methionine alkylated mature human MP52 (SEQ ID No 6) were around 74 min, 42 min, and 30 min in order, showing the earlier elution than that of the fragments of unmodified mature human MP52.

On the other hand, the elution time of other fragments without containing methionine was the same between unmodified and methionine alkylated mature human MP52.

In the amino acid composition analysis, only the number of methionine residues derived from the methionine alkylated mature human MP52 was different from the theoretical values. The N-terminal sequence of these fragments were analyzed by using a sequencer (model 476A; Applied Biosystems) and it is confirmed that the alkylation occurred to methionine residues specifically.

Example 3

Preparation of Mature Human MP52 of which Tryptophane was Allylsulphenylated (1) Allylsulphenylation of Tryptophane Residues of Mature Human MP52 by p-Nitrophenylchloride Twenty-fold molar ratio of p-nitrophenylchloride, which dissolved in 100% acetic acid, was added to the unmodified mature human MP52 (2 mg/ml dissolved in 50% acetic acid) and incubated at room temperature for 1 hour.

(2) Separation of Allylsulphenylated Mature Human MP52

Unmodified mature human MP52 and allylsulphenylated mature human MP52 having the amino acid sequence of SEQ ID No 7 were separated on the basis of a difference in the retention time of column on the reverse phase HPLC. The elution time of allylsulphenylated mature human MP52 delays in comparison with unmodified mature human MP52 on the reverse phase HPLC, which is due to increase in hydrophobic property by allyl sulphenylation. The conditions of separation are as follows; a column employed, a flow rate, and a pump for HPLC were the same as those of Example 1 (2), and column temperature and wavelengths for detection were 40° C., and 214 nm and 365 nm, respectively. For solvent, water containing 0.05% TFA as solution A and acetonitrile containing 0.05% TFA as solution B were used for elution. The elutions of proteins were performed by a linear gradient of solution B from 25% to 60% for 35 minutes after maintaining for five minutes with 25% of solution B. Under the conditions, unmodified mature human MP52 was eluted around 22 min, and in comparison, tryptophane allylsulphenylated mature human MP52 was eluted around 26 min. The difference of elution times between these proteins allows easy separation of them.

(3) Determination of Allylsulphenylation of Tryptophane

After reduction of disulfide bond by the same method described in Example 1, unmodified mature human MP52 of which cysteine residues were alkylated (S-carboxymethylated) and tryptophane allylsulphenylated mature human MP52 were digested by trypsin, and fragments of the digest were separated by C18 reverse phase column. Amino acid positions of the fragments were determined by the amino acid composition analysis.

The trypsin fragment of mature human MP52 containing tryptophane residues was that corresponding to the position from 29th to 56th positions (29–56; containing 32nd and 35th positions of tryptophane) alone shown in SEQ ID No 1. Only the elution time (around 95 min) of a fragment containing tryptophane residue, which is derived from allylsulphenylated mature human MP52 (SEQ ID No 7) delayed in comparison with the elution time (around 84 min) of a fragment derived from the unmodified mature human MP52. On the other hand, the elution time of other fragments without containing tryptophane showed no change. N-terminal sequence analysis showed difference only in tryptophane residue between unmodified and modified mature human MP52.

Example 4

Test of Inhibition of Bone Morphogenetic Activity

BMP-2 antagonistic activity of mature protein of this invention was tested by adding the protein to culture media of MC3T3-E1 cells which are a murine carvarial clonal cell line established by Dr. Kodama et al. and have osteoblast-like properties, or C3H10T ½ cells which are a mesenchymal and multipotent cell line to differentiate to osteoblast, chondrocyte, myocyte, fat cell, according to a culture condition. These cell lines were cultured according to the method described by Dr. Takuwa et al. For the MC3T3-E1 cells, $5\times10^3$ cells per $cm^2$ were inoculated and cultured in α-MEM medium containing 10% fetal bovine serum for three days. After washing cells with the α-MEM medium, the medium was replaced into α-MEM medium containing 0.3% bovine serum albumin. To this medium, the mature protein of the invention with various concentrations and mature rh-BMP-2 (recombinant human BMP-2) were added and then cultured for three days (post-culture). ALPase activity in the cells was measured by calorimetric analysis using p-nitrophenylphosphate as a substrate.

The culture conditions of C3H10T ½ cells were the same as MC3T3-E1 cells except that the medium used for the pre-culture was BME culture medium containing 10% fetal bovine serum and the medium used for the post-culture was BME culture medium containing 2% fetal bovine serum.

FIG. 1 shows the result of ALPase activity by methionine alkylated mature human MP52 in comparison with that by unmodified mature human MP52 in MC3T3-E1 cells. Both proteins were obtained from the difference in the retention time on the reverse phase HPLC in Example 2. In the figure, the solid line with solid circles represents unmodified mature human MP52, the solid line with solid squares represents one-methionine alkylated mature human MP52, the broken line with solid triangles represents two-methionine alkylated mature human MP52, the solid line with open circles represents three-methionine alkylated mature human MP52, the dotted line with open triangles represents four-methionine alkylated mature human MP52, respectively. The solid circles shown in of the Y-axis present activity of cells without treated by any reagent. As shown in FIG. 1, ALPase inducing activity in MC3T3-E1 cells decreased Depending on the progress of alkylation of methionine.

Figure 2B:
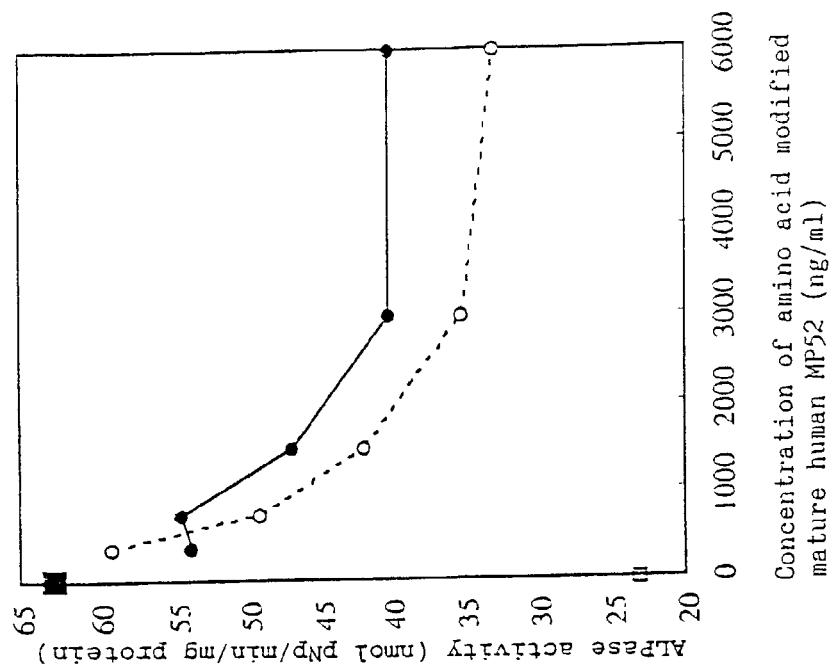
FIG. 2 shows the antagonistic activity of methionine oxidized mature human MP52 and tryptophane allylsulphenylated mature human MP52 in different cell lines. (A) represents their antagonistic activities against mature rh-BMP-2 in C3H10T ½ cells and (B) shows their antagonistic activities against mature human MP52 in MC3T3-E1 cells, respectively. In both figures, the solid line with solid circles represents tryptophane allylsulphenylated mature human MP52 and the dotted line with open circles represents methionine oxidized mature human MP52, respectively. In (A), the solid square shows ALPase activity induced by 300 ng/ml of mature rh-BMP-2 alone in C3H10T ½ cell. In (B) the solid square shows ALPase activity induce by 600 ng/ml of unmodified mature human MP52 alone in MC3T3-E1 cells. Open squares represent the activity in the experiments without any reagent.
Figure 2A:
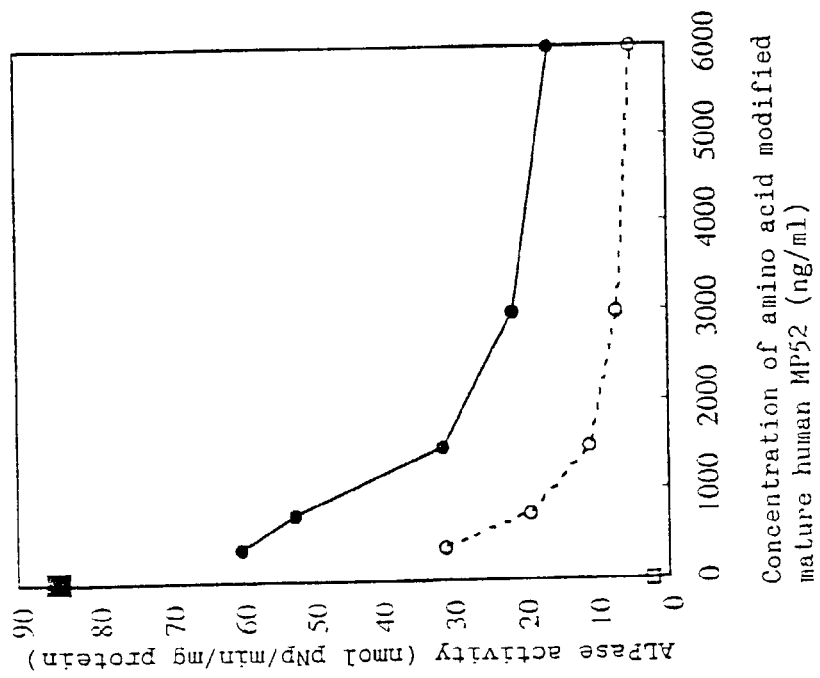

FIG. 2 shows the antagonistic activity of methionine oxidized mature human MP52 obtained in example 1 and tryptophane allylsulphenylated mature human MP52 obtained in example 3 in two different cell lines. FIG. 2 (A) represents an antagonistic activity against mature rh-BMP-2 in C3H10T ½ cells. FIG. 2 (B) shows an antagonistic activity against mature human MP52 in MC3T3-E1 cells. In both figures, the solid line with solid circles represents tryptophane allylsulphenylated mature human MP52 and the dotted line with open circles represents methionine oxidized mature human MP52, respectively. In FIG. 2(A), the solid square shows ALPase activity induced by 300 ng/ml of mature rh-BMP-2 alone in C3H10T ½ cell. In FIG. 2 (B), the solid square shows ALPase activity induced by 600 ng/ml of unmodified mature human MP52 alone in MC3T3-E1 cells. Open squares represent the activity in the experiments without any reagent.

As shown in FIG. 2(A), 300 ng/ml of mature rh-BMP-2 promoted ALPase activity in C3H10T ½ cell about 40 times higher than the control group. The modified mature human MP52 of this invention inhibited the ALPase activity from 1 equivalent- to 20 equivalent-molar in a dose-dependent manner. Moreover, as shown in FIG. 2(B), 600 ng/ml of the unmodified mature human MP52 promoted ALPase activity in MC3T3-E1 cells about 3 times higher than the control group. The amino acid modified mature human MP52 of this invention inhibited the ALPase activity from 1 equivalent- to 10 equivalent-molar in a dose-dependent manner.

The invention claimed is:

1. A BMP antagonist with antagonistic activity against at least one BMP protein selected from the group consisting of MP52, BMP-2, BMP-4 and BMP-7 obtained by replacing at least one methionine or tryptophan residue existing in the receptor binding site of mature human MP52 (SEQ ID NO:1) with a hydrophilic amino acid residue or a polar amino acid residue, or converting said tryptophan residues to a hydrophilic residue by chemical modification.

2. The BMP antagonist according to claim 1, wherein the chemical modification for said tryptophan residue is an allylsulphenylation reaction.

3. The BMP antagonist according to claim 2 in which two tryptophan residues are allylsulphenylated and having the amino acid sequence of SEQ ID NO 7.

4. The BMP antagonist according to claim 1, wherein said mature human MP52 is a dimer protein.

5. A therapeutic agent containing a BMP antagonist according to claim 1.

6. A therapeutic agent for therapy of diseases due to the expression of MP52, BMP-2, BMP-4 and/or BMP-7 containing a BMP antagonist according to claim 1 as an effective ingredient.

7. A method for antagonizing MP52, BMP-2, BMP-4 and BMP-7, comprising administering to a patient in need thereof, an effective amount of a mature modified protein according to claim 1.

8. The method according to claim 7, wherein said patient is suffering from ectopic ossification which is due to ectopic expression of MP62, BMP-2, BMP-4 and/or BMP-7.

9. The method according to claim 7, wherein said patient is suffering from a metabolic disease with calcification.

10. The method according to claim 9, wherein said metabolic disease with calcification is calcification of arterial sclerosis.

11. A BMP antagonist with antagonistic activity against at least one BMP protein selected from the group consisting of MP52, BMP-2, BMP-4 and BMP-7 obtained by converting at least one residue of tryptophan residues existing in the amino acid sequences of mature human BMP-2 (SEQ ID NO 2), mature human BMP-4 (SEQ ID NO 3) or mature human BMP-7 (SEQ ID NO 4) to a hydrophilic residue by chemical modification, or replacing said residues with a hydrophilic amino acid residue or a polar amino acid residue.

12. The BMP antagonist according to claim 11, wherein said mature human BMP-2, mature human BMP-4, or mature human BMP-7 is a dimer protein.

13. A BMP antagonist with antagonistic activity against at least one BMP protein selected from the group consisting of MP52, BMP-2, BMP-4 and BMP-7 obtained by replacing at least one amino acid residue of three hydrophobic amino acid residues, among said hydrophobic amino acid residues relating to a receptor binding site in the amino acid sequences of mature human BMP-2 (SEQ ID NO 2), mature human BMP-4 (SEQ ID NO 3), or mature human BMP-7 (SEQ ID NO 4), which are located in positions corresponding to those of methionine residues located in $30^{th}$, $71^{st}$, and $74^{th}$ positions of the amino acid sequence of mature human MP52 (SEQ ID NO 1) with a hydrophilic amino acid residue or a polar amino acid residue.

14. A BMP antagonist with antagonistic activity against at least one BMP protein selected from the group consisting of MP52, BMP-2, BMP-4 and BMP-7 obtained by converting at least one methionine residue existing in the receptor binding site of mature human MP52 (SEQ ID NO:1) by chemical modification, wherein said chemical modification for said methionine residue is an alkylation reaction.

15. The BMP antagonist according to claim 14, wherein the alkylation reaction is S-carboxymethylation in which at least one methionine residue is S-carboxymethylated and having the amino acid sequence of SEQ ID NO 6.

16. The BMP antagonist according to claim 14, wherein said mature human MP52 is a dimer protein.

17. A therapeutic agent containing a BMP antagonist according to claim 14.

18. A therapeutic agent for therapy of diseases due to the expression of MP52, BMP-2, BMP-4 and/or BMP-7 containing a BMP antagonist according to claim 14 as an effective ingredient.

19. A method for antagonizing MP52, BMP-2, BMP-4 and BMP-7, comprising administering to a patient in need thereof, an effective amount of a mature modified protein according to claim 14.

20. The method according to claim 19, wherein said patient is suffering from ectopic ossification which is due to ectopic expression of MP52, BMP-2, BMP-4 and/or BMP-7.

21. The method according to claim 19, wherein said patient is suffering from a metabolic disease with calcification.

22. The method according to claim 21, wherein said metabolic disease with calcification is calcification of arterial sclerosis.

23. A mature modified protein obtained by replacing at least one methionine residue at position 30, 71 or 74 or at least one tryptophan residue existing in mature human MP52 (SEQ ID NO:1) with a hydrophilic amino acid residue or a polar amino acid residue, or converting said tryptophan residues to a hydrophilic residue by chemical modification, wherein said mature modified protein has antagonistic activity against at least one BMP protein selected from the group consisting of MP52, BMP-2, BMP-4 and BMP-7.

24. A mature, modified protein obtained by replacing at least one methionine or at least one tryptophan residue existing in the receptor binding site of mature human MP52 (SEQ ID NO 1) with a hydrophilic amino acid residue or a polar amino acid residue, or converting said tryptophan residues to a hydrophilic residue by chemical modification, wherein said mature modified protein has antagonistic activity against at least one BMP protein selected from the group consisting of MP52, BMP-2, BMP-4 and BMP-7.

* * * * *

UNITED STATES PATENT AND TRADEMARK OFFICE
CERTIFICATE OF CORRECTION

PATENT NO. : 7,132,397 B1 Page 1 of 1
APPLICATION NO. : 09/806368
DATED : November 7, 2006
INVENTOR(S) : Katsuura et al.

It is certified that error appears in the above-identified patent and that said Letters Patent is hereby corrected as shown below:

Column 2, line 41, delete "reverse chase HPLC" and insert --reverse phase HPLC--

Column 3, line 18, delete "chat" and insert --that--

Column 7, line 6, delete "$21^{st}$" and insert --$31^{st}$--

Column 13, line 26, delete "calorimetric" and insert --colorimetric--

Column 14, line 9, delete "Depending" and insert --depending--

Column 21, line 65, in Claim 8, delete "MP62" and insert --MP52--

Signed and Sealed this

Twentieth Day of March, 2007

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 119
<212> TYPE: PRT
<213> ORGANISM: Homo sapiens
<220> FEATURE:
<221> NAME/KEY: CHAIN
<222> LOCATION: (1)..(119)
<223> OTHER INFORMATION: Mature MP52
<300> PUBLICATION INFORMATION:
<302> TITLE: NOVEL PROTEIN AND PROCESS FOR PRODUCING THE SAME
<309> DATABASE ENTRY DATE:
<310> PATENT DOCUMENT NUMBER: WO9633215
<311> PATENT FILING DATE: 1996-04-19
<312> PUBLICATION DATE: 1996-10-24
<313> RELEVANT RESIDUES: (1)..(119)

<400> SEQUENCE: 1

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30
```

-continued

```
Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
                100                 105                 110

Val Glu Ser Cys Gly Cys Arg
            115

<210> SEQ ID NO 2
<211> LENGTH: 114
<212> TYPE: PRT
<213> ORGANISM: Homo sapiens
<220> FEATURE:
<221> NAME/KEY: CHAIN
<222> LOCATION: (1)..(114)
<223> OTHER INFORMATION: Mature BMP-2
<300> PUBLICATION INFORMATION:
<302> TITLE: NOVEL OSTEOINDUCTIVE COMPOSITIONS
<309> DATABASE ENTRY DATE:
<310> PATENT DOCUMENT NUMBER: WO8800205
<311> PATENT FILING DATE: 1987-06-30
<312> PUBLICATION DATE: 1988-01-14
<313> RELEVANT RESIDUES: (1)..(114)

<400> SEQUENCE: 2

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
                100                 105                 110

Cys Arg

<210> SEQ ID NO 3
<211> LENGTH: 116
<212> TYPE: PRT
<213> ORGANISM: Homo sapiens
<220> FEATURE:
<221> NAME/KEY: CHAIN
<222> LOCATION: (1)..(116)
<223> OTHER INFORMATION: Mature BMP-4
<300> PUBLICATION INFORMATION:
<301> AUTHORS: Wozney, JM et al.
<302> TITLE: NOVEL REGULATORS OF BONE FORMATION MOLECULAR CLONES AND
       ACTIVITIES
<303> JOURNAL: SCIENCE
<304> VOLUME: 242
<305> ISSUE: 4885
<306> PAGES: 1528-1534
<307> DATE: 1988-12-16
<308> DATABASE ACCESSION NUMBER: GENBANK/M22490
```

-continued

```
<309> DATABASE ENTRY DATE: 1994-10-31

<400> SEQUENCE: 3

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
            35                  40                  45

Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
                100                 105                 110

Cys Gly Cys Arg
        115

<210> SEQ ID NO 4
<211> LENGTH: 139
<212> TYPE: PRT
<213> ORGANISM: Homo sapiens
<220> FEATURE:
<221> NAME/KEY: CHAIN
<222> LOCATION: (1)..(139)
<223> OTHER INFORMATION: Mature BMP-7
<300> PUBLICATION INFORMATION:
<301> AUTHORS: OZKAYNAK, E. et al.
<302> TITLE: OP-1 cDNA encodes an osteogenic protein in the TGF-beta.
<303> JOURNAL: EMBO J.
<304> VOLUME: 9
<305> ISSUE: 7
<306> PAGES: 2085-2093
<307> DATE: 1990-07-01
<308> DATABASE ACCESSION NUMBER: EMBL/ X51801
<309> DATABASE ENTRY DATE: 1994-10-31

<400> SEQUENCE: 4

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
                20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 5
```

```
<211> LENGTH: 119
<212> TYPE: PRT
<213> ORGANISM: Homo sapiens
<220> FEATURE:
<221> NAME/KEY: CHAIN
<222> LOCATION: (1)..(119)
<223> OTHER INFORMATION: Mature MP52 protein. Note : 30th, 71st, 74th
      and 111th Met are modified to Met sulfoxide.

<400> SEQUENCE: 5

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115

<210> SEQ ID NO 6
<211> LENGTH: 119
<212> TYPE: PRT
<213> ORGANISM: Homo sapiens
<220> FEATURE:
<221> NAME/KEY: CHAIN
<222> LOCATION: (1)..(119)
<223> OTHER INFORMATION: Mature MP52 protein. Note : 30th and/or 71st
      and/or 74th and/or 111th Met are modified to s-carboxymethyl Met.
<220> FEATURE:
<221> NAME/KEY: CHAIN
<222> LOCATION: (1)..(119)
<223> OTHER INFORMATION: Mature MP52 protein. Note : 30th and/or 71st
      and/or 74th and/or 111th Met are modified to s-carboxymethyl Met.

<400> SEQUENCE: 6

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115

<210> SEQ ID NO 7
```

-continued

```
<211> LENGTH: 119
<212> TYPE: PRT
<213> ORGANISM: Homo sapiens
<220> FEATURE:
<221> NAME/KEY: CHAIN
<222> LOCATION: (1)..(119)
<223> OTHER INFORMATION: Mature MP52 protein. Note :32nd and 35th Trp
      are modified to allylsulphenyl Trp.

<400> SEQUENCE: 7

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
            35                  40                  45

Gly Leu Cys Glu Phe Pro Leu Arg Ser His Leu Glu Pro Thr Asn His
        50                  55                  60

Ala Val Ile Gln Thr Leu Met Asn Ser Met Asp Pro Glu Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
            115
```